(12) United States Patent
Haaja et al.

(10) Patent No.: US 10,511,193 B2
(45) Date of Patent: Dec. 17, 2019

(54) DEVICE WITH A RECEIVING ANTENNA AND A RELATED POWER TRANSFER SYSTEM

(71) Applicant: SYNOSTE OY, Espoo (FI)

(72) Inventors: Juha Kalevi Haaja, Espoo (FI); Kevin Lambertus Hubertus Salden, Einighausen (NL); Harri Olavi Hallila, Helsinki (FI); Jorge Luiz Duarte, Eindhoven (NL); Antti Gabriel Ritvanen, Helsinki (FI)

(73) Assignee: Synoste Oy (FI)

( * ) Notice: Subject to any disclaimer, the term of this patent is extended or adjusted under 35 U.S.C. 154(b) by 266 days.

(21) Appl. No.: 15/519,644

(22) PCT Filed: Sep. 30, 2015

(86) PCT No.: PCT/FI2015/050648
§ 371 (c)(1),
(2) Date: Apr. 17, 2017

(87) PCT Pub. No.: WO2016/059289
PCT Pub. Date: Apr. 21, 2016

(65) Prior Publication Data
US 2017/0244287 A1     Aug. 24, 2017

(30) Foreign Application Priority Data
Oct. 17, 2014   (EP) ..................... 14189377

(51) Int. Cl.
*H02J 50/12* (2016.01)
*A61B 17/72* (2006.01)
(Continued)

(52) U.S. Cl.
CPC .......... *H02J 50/12* (2016.02); *A61B 17/7216* (2013.01); *H01F 38/14* (2013.01);
(Continued)

(58) Field of Classification Search
CPC . H02J 5/005; H02J 7/025; H02J 17/00; B60L 11/182; B60L 53/12; H01F 38/14;
(Continued)

(56) References Cited

U.S. PATENT DOCUMENTS

2007/0150009 A1   6/2007 Kveen et al.
2008/0051854 A1*  2/2008 Bulkes ............... A61N 1/37211
                                                      607/60
(Continued)

FOREIGN PATENT DOCUMENTS

WO   2006/127355 A2   11/2006
WO   2013/098784 A1   7/2013

OTHER PUBLICATIONS

Ota, Y. et al., "Wireless Power Transfer by Low Coupling Electromagnetic Induction—LC booster", 2012 IEEE MTT-S International Microwave Workshop Series on Innovative Wireless Power Transmission: Technologies, Systems, and Applications (IMWS), May 10-11, 2012, pp. 175-178 (Tohoku University, Sendai, Miyagi, 980-8579, Japan.

(Continued)

*Primary Examiner* — Rexford N Barnie
*Assistant Examiner* — David A Shiao
(74) *Attorney, Agent, or Firm* — Renner Kenner Greive Bobak Taylor & Weber

(57) ABSTRACT

The present invention is about a device with a receiving antenna (110), wherein the receiving antenna (110) comprises a secondary coil (112), and being arranged for inductively connecting to a transmitting antenna (200) comprising a primary coil (202). The device of the invention is characterized in that the receiving antenna (110) further comprises a tertiary coil (114) arranged to have connection to a load in the device; and a capacitor (142) to which the secondary coil (112) is connected; and there is an encapsulation (120)

(Continued)

comprising a low liquid permeability and non-conductive material encapsulating at least a part of the receiving antenna (110). Additionally, the present invention is about a power transfer system.

8 Claims, 2 Drawing Sheets

(51) Int. Cl.
*H01Q 1/24* (2006.01)
*H01Q 7/08* (2006.01)
*H01F 38/14* (2006.01)
*A61B 1/00* (2006.01)
*A61N 1/378* (2006.01)
*A61M 1/12* (2006.01)

(52) U.S. Cl.
CPC .............. *H01Q 1/248* (2013.01); *H01Q 7/08* (2013.01); *A61B 1/00029* (2013.01); *A61M 1/127* (2013.01); *A61N 1/3787* (2013.01)

(58) Field of Classification Search
CPC ............. A61B 1/00029; A61N 1/3787; A61M 2205/8243
See application file for complete search history.

(56) References Cited

U.S. PATENT DOCUMENTS

| | | | |
|---|---|---|---|
| 2009/0270948 A1 | 10/2009 | Nghiem et al. | |
| 2011/0009924 A1 | 1/2011 | Meskens | |
| 2011/0080052 A1* | 4/2011 | Sato | H02J 5/005 307/104 |
| 2011/0101788 A1 | 5/2011 | Sun et al. | |
| 2012/0150291 A1* | 6/2012 | Aber | H02J 7/025 623/3.14 |
| 2012/0194127 A1* | 8/2012 | Kobayashi | H01G 9/155 320/108 |
| 2013/0057364 A1* | 3/2013 | Kesler | H01Q 7/00 333/219.2 |
| 2013/0241306 A1 | 9/2013 | Aber et al. | |
| 2014/0167524 A1* | 6/2014 | Oodachi | H01F 27/346 307/104 |
| 2014/0240947 A1* | 8/2014 | Nakamura | B60L 53/36 361/818 |
| 2014/0265621 A1* | 9/2014 | Wong | H02J 5/005 307/104 |
| 2014/0305722 A1* | 10/2014 | Ichikawa | B60L 53/38 180/65.31 |
| 2015/0214747 A1* | 7/2015 | Abe | H01F 38/14 307/104 |
| 2016/0067497 A1* | 3/2016 | Levine | A61B 5/6877 607/62 |

OTHER PUBLICATIONS

Johari, R. et al., "Analysis and Practical Considerations in Implementing Multiple Transmitters for Wireless Power Transfer via Coupled Magnetic Resonance", IEEE Transactions on Industrial Electronics, Apr. 2014, vol. 61, No. 4, pp. 1774-1783.
European Search Report (Application No. 14189377.6) (dated Apr. 5, 2016—6 pages).

* cited by examiner

DEVICE WITH A RECEIVING ANTENNA AND A RELATED POWER TRANSFER SYSTEM

The invention relates to a device with a receiving antenna. Especially, the invention relates to a device wherein the receiving antenna comprises a secondary coil, a tertiary coil and a load, and may be inductively connected to an external transmitting antenna. Further, the invention is especially for implantable devices.

Implantable electronic devices have recently become an important tool for monitoring, measuring and triggering physiological responses in the human body. For the increasing survival rate as well as quality of life for the patient, it is essential to find embodiments which fulfill the strict requirements for the stability, miniaturization, functionality and lower energy consumption of implantable electronic devices.

It is known from prior art that an implant is equipped with a connector for a receiver unit. The receiver unit can be contactless activated from an external transmitter unit.

It is known a receiving antenna, which is used in the limb lengthening treatment of the lower legs. The inductive power transfer configuration in the application area is to use a subcutaneously implanted antenna. This kind of configuration allows for short transfer distance and good and efficient coupling. However, the implantation of the antenna is difficult, time consuming and increases the chances of possible complications.

It is disclosed in the publication US 20040023623 a device for controlling, regulating or putting an active implant into operation. In the publication a distraction device is implanted with a receiver unit to which data or power can be supplied from the outside via a transmitter unit.

For the concerning efficient, contactless electromagnetic energy transfer between windings, the miniaturization of the receiving part is essential. The receiving winding is restrained to much smaller dimensions than the sending one. This results in low magnetic coupling between coils. In a typical approach of prior art, the receiving coil is assembled around ferromagnetic material, e.g. a ferrite rod. It is to be noted, that the Ferrite should not be brought into magnetic saturation. The saturation may cause unacceptable losses and temperature rise.

Further, to facilitate the energy transfer, the operation frequency should be as high as possible. With higher frequency of the power transfer the magnetic coupling is better and consequently, the required dimensions for the passive components are smaller.

By considering a body implant, the geometry of the sending winding is fairly fixed as the application has limitations for transmitting coil, for gaining the desirable power transfer. The dimensions of the receiving winding will be about twenty times smaller, or even less, than the ones of the sending part.

A typical way of prior art is to connect the receiving antenna directly to the resistive load, without any reactive power compensation. This enables a smaller receiving part and housing with limited volume can be used. The direct excitation of the sending windings requires a high-voltage power source together with a relatively high current. Only by this, the magnetization of the sending coils can be reached. However, the high-voltage and high-current puts serious limitations on the attainable frequency for the energy transfer, since the required power supply will be quite voluminous, compromising seriously the portability of the converter.

A more effective approach towards miniaturization is to compensate the self-inductance of the windings by series-capacitors. Due to series resonance, the voltage of the windings terminals is high, but the necessary power supply voltage is quite low, which drastically reduces the volume of the converter. The value of the self-inductance of each winding is easily determined and does not change with the mutual coupling between the coils.

For accommodating the capacitor for an available volume, the winding dimensions should somehow be changed. Reducing the number of turns causes reduction of the coupling, which further causes requirements of higher voltage and a larger value and volume of the associated compensating capacitor. On the other hand, by raising the number of winding turns, the ferrite material may be brought to saturation.

Among the problems of the preferable dimensioning, there may be problems with finding commercially available components suitable for the usage.

In order to facilitate contactless transfer of electrical energy between two windings with weak magnetic coupling, the addition of a third winding is suggested to allow the practical matching of component ratings.

With the third winding, the real and reactive current components in the receiving part can be separated for a great deal. As now, the current through the compensating capacitor is not the same as the current through the load, flexibility for designing the load winding is achieved. This multiplies the possibilities for choosing the proper number of turns and geometry as well as voltage rate of the compensating capacitor.

The prior art embodiments have several problems. They are struggling with at least some of the problems such as bad efficiency, non-biocompatible components, inefficient coil arrangements for enabling the encapsulation, hermetic encapsulations and leakage into the implant through the wiring.

The prior art problems are solved by a device with a receiving antenna, wherein the receiving antenna comprises a secondary coil and a tertiary coil. The tertiary coil is arranged to have connection to a load in the device. The receiving antenna is arranged for inductively connecting to a transmitting antenna comprising a primary coil. The device of the invention is characterized in that the receiving antenna further comprises a capacitor to which the secondary coil is connected. Further, there is an encapsulation comprising a low liquid permeability and non-conductive material encapsulating at least a part of the receiving antenna such that the windings of the tertiary coil are outside the encapsulation.

Another realization for the solution is a power transfer system including a transmitting antenna and a device with the above mentioned features located such that they are inductively connected.

The device of the present invention is especially usable as an implantable device, but is also usable in corrosive circumstances as well as in other challenging environments, wherein the antenna is e.g. molded into the surrounding structure.

Here, the term "capacitor" should be understood to mean any electronic element with capacitive features.

To avoid the compensation of any common magnetic flux linkage and losing the connection to the primary coil, the secondary coil and the tertiary coil should not be perfectly coupled. The leakage flux of the tertiary and secondary coils is the way to transfer energy from the primary coil. However, the magnetization of the possible ferrite material in the tertiary and secondary coils is due to the effective magnetizing field as created by the two currents together. Therefore, the individual currents of the tertiary and secondary coils may be larger than the load current alone.

The mutual coupling between the secondary and tertiary coils becomes an extra design parameter and the trade-off between the number of turns, winding losses, magnetic saturation, capacitor voltage stress and sending winding voltage can be reached on the basis of the three winding combination.

As the introduction of the ferrite as well the improvement of the coupling cause more non-biocompatible components, e.g. capacitor and solder, there is need for hermetic sealing which encapsulates the non-biocompatible components.

In one embodiment of the invention, the tertiary coil connected to the load would be the centermost coil of the implantable structure. In this case, however, the capacitor is located outside of the coil and the ferrite inside the coil. The usage of two separate hermetic packages is needed, one for the capacitor and one for the ferrite core. Alternatively, the whole receiving antenna would be encapsulated and the vias, especially hermetic vias, for connection to the implant should be introduced.

It is another preferred embodiment of the invention, that the secondary coil is located under the tertiary coil and the construction. In this case, a single hermetic package for the secondary circuit can be used.

In one embodiment of the invention, the problems related to an antenna that has to be implanted separately, can be solved by having an antenna that is integrated into the end of the intramedullary nail or such. This, however, leads into a long transfer distance and primary coil diameters of 200-250 mm are common. Also, the diameter of the integrated antenna is typically small, in the range of 7-9 mm due to the limited size of the intramedullary canal.

Further, in the receiving antenna, there may be an element including ferromagnetic material, for focusing the magnetic field of the transmitting antenna into the receiving antenna.

The mentioned element including ferromagnetic material may typically be a ferrite core, but it is also possible to use any other materials or mixtures that may have similar effects on the magnetic field. The introduction of ferrite core helps with focusing the magnetic field.

Additionally, the secondary coil may be arranged to couple to the tertiary coil through the element including ferromagnetic material for creating a transformer between the secondary coil and the tertiary coil.

Here, the term "transformer" means any kind of formulation of mutual inductance between the elements.

Furthermore, the secondary coil and the capacitor may constitute a secondary circuit and the encapsulation may be arranged to encapsulate substantially the complete secondary circuit with the element including ferromagnetic material constituting one package.

The encapsulation may mainly and preferably substantially purely consist of the low liquid permeability and non-conductive material. The low liquid permeability material may typically be material capable of providing hermetic encapsulation.

Alternatively, the encapsulation may be arranged to encapsulate substantially the complete receiving antenna and to have vias, especially hermetic vias, for the connection to the load.

Here, the term "via" means any kind of physical and/or electrical connection embodied through the encapsulation. In some connections, they may be called as feed throughs or such. For generating this kind of connection, there should be made some kind of hole or opening for the connection wires or leads on the encapsulation, wrapping, casing or packaging.

In a preferred embodiment of the invention, the secondary coil and the tertiary coil are arranged concentric one upon the other such that they couple. Alternatively, the secondary coil and the tertiary coil may be arranged next to each other or side by side such that they couple.

The device may be an intramedullary nail. In that case, the load is a distraction device. The device may also be a pacer or any other implantable device for medical treatment or such.

It is another preferred embodiment of the invention, wherein the said low liquid permeability and non-conductive material of the encapsulation comprises one of ceramics and plastic.

The typical preferred materials for the encapsulation may be e.g. PEEK, Parylene C, Polyurethane or glass.

It is still another embodiment of the invention, wherein the receiving antenna is arranged to resonate substantially at the same frequency as the transmitting antenna.

The Q-factor of the circuit has a known effect on the peak of the resonating circuit. When considering the width of the amplitude peak in frequency domain, the larger Q-factor causes the −3 dB band to be narrower. With a very narrow band the frequencies of the two circuits have to, of course, be closer to each other to resonate together. For example, a circuit with normal frequency of 300 kHz may resonate with e.g. circuits of frequencies on the range of 250-350 kHz, 260-340 kHz, 275-325 kHz, 290-310 kHz, or even 299.5-300.5 kHz, depending on the Q-factor. Further, the closer the frequencies are, the stronger the circuits will resonate together.

Due to the distance between the transmitting and receiving antennas the coupling factor between them is typically very weak. The first step to improve the coupling between the antennas and their coils, is to use a ferrite or such in the receiving antenna in order to focus the magnetic field of the transmitting antenna into the receiving antenna. This, however, does not increase the coupling factor to the levels required for feasible operations. By using a resonant coil and the primary coil of the transmitting antenna, the needed power for driving the primary coil is reduced.

The electrical solution, however, leaves further problems on the application. The embodiment now includes two non-biocompatible components, the ferrite, which typically is of MnZn, and a capacitor, which may be of various materials.

The non-biocompatible materials of the antenna have to be somehow encapsulated.

In the following, the invention is described in more detail with reference to the attached drawings, wherein.

Figure 1:
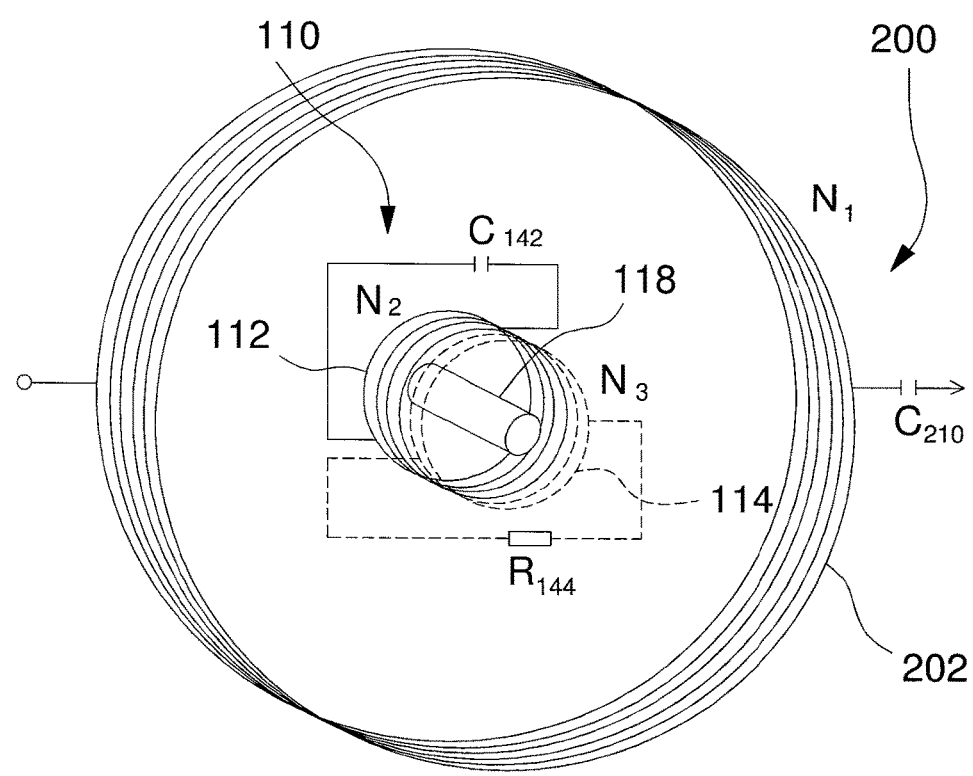
FIG. 1 shows the assembly of three coils
Figure 3:
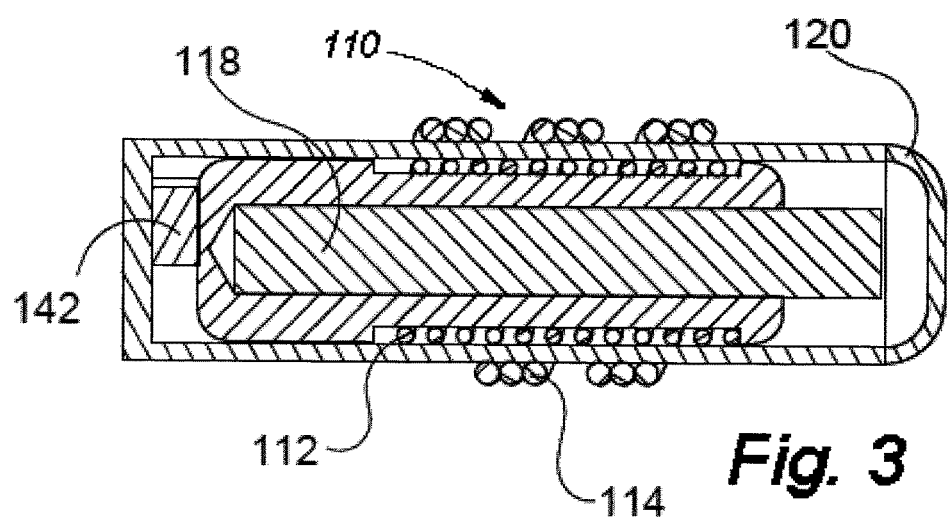

FIG. 3 shows a cross-section view of the receiving antenna configuration with an encapsulation FIG. 1 shows the assembly of the three coils 112, 114 and 202. The primary coil 202 is connected in series with a compensating capacitor 210 which together form a transmitting antenna 200. Secondary coil 112 and tertiary coil 114 are around an element including ferromagnetic material e.g. a ferrite rod 118 and a capacitor 142 and a resistance 144 are connected to the terminals.

Figure 2:
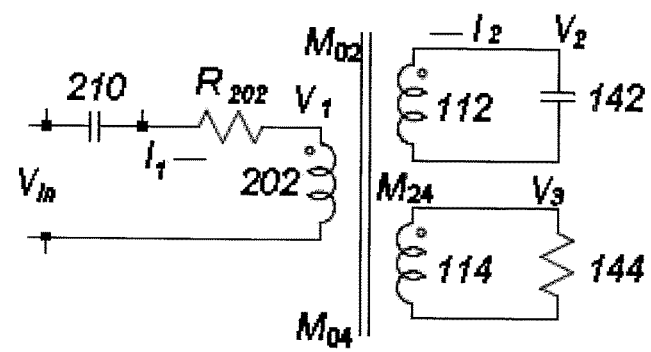
FIG. 2 shows an equivalent circuit of the assembly in FIG. 1

The generation of mutual inductances is visible in equivalent circuit of FIG. 2.

The approach of the FIGS. 1 and 2 is especially advantageous for applications where the dimensions of the primary and secondary coils 202 and 112 are far different from each other, which leads to a weak magnetic coupling.

The geometric dimensions of the primary coil 202 are determined by the needs of the application. The number of turns $N_1$ imposes the value of the coil windings self-inductance $L_{202}$, and a trade-off has to be found between the required current through $L_{202}$ and the dissipated power in the coil windings resistance $R_{202}$.

In a practical implementation, it is convenient to drive the primary coil windings with a block-shaped voltage waveform as generated by half-bridge converters with constant dc bus voltage $V_{dc}$, and constant frequency $f_{in}$. The rms fundamental component of the block shaped voltage $V_{in}$ is given by the equation 1 as $$V_{in} = \frac{2}{\pi\sqrt{2}} V_{dc} \qquad (1)$$

The primary winding is then connected in series with a capacitor $C_{210}$, whose value should be chosen such that $$\frac{1}{\sqrt{L_{202}C_{210}}} = 2\pi f_{in} \qquad (2)$$

This means that the self-inductance of the primary winding is series-compensated, independent of the relative position of the other windings.

The secondary and tertiary windings are tightly wounded around a small ferrite rod, with number of turns equal to $N_2$ and $N_3$ respectively. It is assumed that both windings have much smaller radii than the primary winding. The secondary winding, with self-inductance $L_{112}$, is connected at its terminals to a capacitor $C_{142}$. Finally, the tertiary winding is connected to a resistance $R_{144}$, in which power dissipation is expected to occur according to the needs of the application.

By considering fundamental harmonic components, the voltage/current phasor relationships for the three windings is found to be $$V_1 = j\omega L_{202} I_1 + j\omega M_{02} I_2 + j\omega M_{04} I_3 = Z_{11} I_1 + Z_{12} I_2 + Z_{13} I_3 \qquad (3)$$

$$V_2 = j\omega M_{02} I_1 + j\omega L_{112} I_2 + j\omega M_{24} I_3 = Z_{12} I_1 + Z_{22} I_2 + Z_{23} I_3 \qquad (4)$$

$$V_3 = j\omega M_{04} I_1 + j\omega M_{24} I_2 + j\omega L_{114} I_3 = Z_{13} I_1 + Z_{23} I_2 + Z_{33} I_3 \qquad (5)$$

where $\omega = 2\pi f_{in}$, and $M_{02}$ is the mutual inductance between the primary winding and secondary winding, $M_{04}$ is the mutual inductance between the primary winding and tertiary winding and $M_{24}$ is the mutual inductance between the secondary winding and tertiary winding.

By connecting a capacitor to the secondary winding terminals, it follows from the notation on FIG. 2 that $$V_2 = V_{C_{142}} = \frac{-1}{j\omega C_{142}} I_2 = -Z_{C_{142}} I_2 \qquad (6)$$

The value of $C_{142}$ should be chosen as $$C_{142} = 1/\omega^2 L_{112}(1 - k_{24}^2) \qquad (7)$$

where $k_{24} = M_{24}/\sqrt{L_{112} L_{114}}$ represents the coupling between secondary and tertiary windings. By this way the self-inductances $L_{112}$ and $L_{114}$ and the mutual inductance $M_{24}$ are fully compensated by $C_{142}$ when $I_1 = 0$.

The values of $N_2$ and $N_3$ impose the windings self- and mutual inductances $L_{112}$, $L_{114}$, $M_{24}$ and may be determined in such a way to avoid saturation of the ferrite rod and to limit the maximal voltage on $C_{142}$ at full load.

For example, if $P_{144}$ is the desired power that should be dissipated in $R_{144}$, the resistance connected at the tertiary winding, it implies the rms tertiary current $$I_3 = \sqrt{\frac{P_{144}}{R_{144}}} \qquad (8)$$

From the conventions in FIG. 2 follows that $V_3 = -R_{144} I_3$ and $V_2 = -Z_{C_{142}} I_2$. Therefore, after some manipulations with the voltage/current phasor relationships above, the rms primary and secondary currents are found to be $$I_1 = \frac{-1}{\Delta}[(Z_{22} + Z_{C_{142}})(R_{144} + Z_{33}) - Z_{33}^2] I_3 \qquad (9)$$

$$I_2 = \frac{1}{\Delta}[Z_{12}(R_{144} + Z_{33}) - Z_{13} Z_{23}] I_3 \qquad (10)$$

where $$\Delta = Z_{13}(Z_{22} + Z_{C_{142}}) - Z_{23} Z_{12} \qquad (11)$$

When all the rms currents are known, the rms value of the fundamental component of the input voltages is easily determined with $$V_{C_{210}} = Z_{C_{210}} I_1 = \frac{1}{j\omega C_{210}} I_1 \qquad (12)$$

$$V_{in} = V_{C_{210}} = R_{202} I_1 = V_1 \qquad (13)$$

which yields the dc bus voltage level $$V_{dc} = \frac{\pi\sqrt{2}}{2} V_{in} \qquad (14)$$

necessary to create a block-shaped voltage waveform by means of a half-bridge converter. Further the peak flux density on the ferrite rod is given by $$\Psi_2 = \frac{\sqrt{2}}{N_2}(|M_{02} I_1 + L_{112} I_2 + M_{24} I_3|) \qquad (15)$$

$$B_{max2} = \frac{\Psi_2}{A_2} \qquad (16)$$

where $A_2$ is the cross-sectional area of the ferrite core. All together, the power transfer efficiency is found to become $$\vartheta = \frac{R_{144}|I_3|^2}{R_{202}|I_1|^2 + R_{144}|I_3|^2} \qquad (17)$$

The FIG. 3 shows one embodiment of the encapsulation 120 of the invention. In this context, the material of the encapsulation is chosen to be hermetic and non-conductive, which usually means ceramics. The material used to encapsulate electronics should possess a high resistivity and high dielectric strength.

The proper encapsulation materials may comprise metals, such as titanium and its alloys, biograde stainless steel, cobalt based alloys, tantalum, niobium, titanium-niobium alloys, nitinol, MP35N, and some noble metals. They may also comprise glass, ceramics. Additionally, polymeric materials, such as epoxies, silicones, polyurethanes, polyimides, silicon-polyimides, parylenes, polycyclic-olefins, silicon-carbons, bentzocyclobutenes and liquid crystal polymeres, are applicable.

Ceramic encapsulation 120 of the ferrite 118 is straight forward. However, the encapsulation the capacitor 142 turns to be problematic. The capacitor would require hermetic vias to it in order to connect it to the secondary coil 112. These are not economically feasible with high currents.

The space limitations in implantable applications, especially in an intramedullary device, are evident. Therefore, it would be beneficial to limit the amount of different encapsulation layers. This can be realized by encapsulating the complete secondary coil 112 and ferrite into same package.

Typically in the electrical configuration, the secondary coil 112 is on the top of the tertiary coil 114. This makes the encapsulation 120 into a single package difficult.

The coil wires should be routed from the tertiary coil 114 to the driven load. However, by flipping the configuration such, that the secondary coil will be the centermost coil in the assembly, the problems of the wire routing can be solved. The windings of the tertiary coil 114 can now be set on the top of the encapsulation 120.

Biocompatibility is defined as the ability of a material to perform with an appropriate host response in a specific application. When using a biocompatible material, such as gold, platinum, silver or gold-platted silver, for the windings of the tertiary coil 114, a long-term biocompatible solution is reached. Further, in the case of encapsulated active implants it is generally desirable, that the implant is non-toxic, noncarcinogenic and nonthrombogenic. Furthermore, the encapsulation should not cause any mechanical irritation in the surrounding tissues.

Further, the liquid leak inside the implant has to be prevented. Due to the need of connecting the windings of the tertiary coil 114 into the load some cables need to be routed. The introduction of body fluids has to be prevented. The fluids may reach the implant through capillary effect as the cables of the receiving antenna allow the direct path there. The physiological fluids contain several organic and inorganic materials and cellular components such as salts, enzymes, hormones, proteins and entire cells, which make the human body one of the most corrosive environments.

The prevention of the body fluids leakage may be achieved in several ways. In one embodiment of the invention, a hermetic via connector may be used to connect to the receiving antenna 110. Alternatively, the receiving antenna 110 may be over-molded with a polymer to stop liquid from penetrating into the cables. Further, the receiving antenna 110 may be encapsulated into a second hermetic packaging. Alternatively, the receiving antenna 110 may be encapsulated into a thermoplastic.

In a preferred embodiment of the invention an ultrasonically sealed encapsulation for the receiving antenna and a lipseal would be used. This ultrasonic welding of thermoplastic prevents the leakage from the interface of the antenna.

The encapsulation 120 may include an ultrasonic or laser welding for preventing any leakage. There may also be a further casing enclosing the entire receiving antenna 110. The further casing is preferably plastic encapsulation and it may also include an ultrasonic welding for preventing any leakage.

LIST OF REFERENCE MARKINGS 110 receiving antenna
112 secondary coil
114 tertiary coil
118 element including ferromagnetic material
120 encapsulation
142 capacitor
144 resistance
200 transmitting antenna
202 primary coil
210 compensating capacitor
$L_{202}$ self-inductance of primary coil windings
$L_{112}$ self-inductance of secondary coil windings
$L_{114}$ self-inductance of the tertiary coil windings
$R_{202}$ resistance of the primary coil windings
$R_{144}$ resistance of the resistor in connection to the tertiary windings
$C_{210}$ capacitance of the capacitor in connection to the primary coil windings
$C_{142}$ capacitance of the capacitor in connection to the secondary coil windings
$M_{02}$ mutual inductance between the primary winding and secondary winding
$M_{04}$ mutual inductance between the primary winding and tertiary winding
$M_{24}$ mutual inductance between the secondary winding and tertiary winding
$V_{dc}$ dc bus voltage
$f_{in}$ constant frequency
$V_{in}$ block shaped voltage
$V_1$ voltage of primary winding
$V_2$ voltage of secondary winding
$V_3$ voltage of tertiary winding
$V_{C_{142}}$ voltage of capacitor in connection to the secondary coil windings
$V_{C202}$ voltage of capacitor in connection to the primary coil windings
$P_{144}$ power dissipated in a resistor
$N_1$ number of turns in primary windings
$N_2$ number of turns in secondary windings
$N_3$ number of turns in tertiary windings
$k_{24}$ coupling between secondary and tertiary windings
$I_1$ current primary winding
$I_2$ current secondary winding
$I_3$ current tertiary winding
θ power transfer efficiency
ψ2 peak flux
$B_{max2}$ peak flux density
$A_2$ cross-sectional area of an element including ferromagnetic material
$Z_{11}$ impedance factor
$Z_{12}$ impedance factor
$Z_{13}$ impedance factor
$Z_{22}$ impedance factor
$Z_{23}$ impedance factor
$Z_{33}$ impedance factor $Z_{C_{142}}$ impedance factor
$Z_{C_{202}}$ impedance factor

The invention claimed is:

1. A device with a receiving antenna, wherein the receiving antenna comprises a secondary coil, and is arranged for inductively connecting to a transmitting antenna comprising a primary coil (202); wherein the receiving antenna further comprises:
 a tertiary coil arranged to have a connection to a load in the device;
 a capacitor to which the secondary coil is connected; and
 an encapsulation comprising a low liquid permeability and non-conductive material encapsulating at least the secondary coil and the capacitor such that the tertiary coil is being wound around the encapsulation and the secondary coil; and
wherein the receiving antenna is arranged to resonate substantially at the same frequency as the transmitting antenna; and
wherein the entire receiving antenna is enclosed by a casing.

2. The device of claim 1, wherein in the receiving antenna, there is an element including ferromagnetic material, for focusing the magnetic field of the transmitting antenna into the receiving antenna.

3. The device of claim 2, wherein the secondary coil is arranged to couple to the tertiary coil through the element for creating a transformer between the secondary coil and the tertiary coil.

4. The device of claim 1, wherein the secondary coil and the tertiary coil are arranged concentric one upon the other such that they couple.

5. The device of claim 1, wherein the secondary coil and the tertiary coil are arranged next to each other such that they couple.

6. The device of claim 1, wherein the said low liquid permeability and non-conductive material of the encapsulation comprises one of ceramics and plastic.

7. The device of claim 1, wherein at least one of the encapsulation and the casing includes an ultrasonic or laser welding for preventing any leakage.

8. A power transfer system including a transmitting antenna and the device of claim 1 located such that they are inductively connected.

* * * * *